US00PP15545P2

(12) United States Plant Patent
Brown

(10) Patent No.: US PP15,545 P2
(45) Date of Patent: Feb. 8, 2005

(54) ***DIASCIA* PLANT NAMED 'CODILAV'**

(50) Latin Name: *Diascia×hybrida*
Varietal Denomination: Codilav

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 7 days.

(21) Appl. No.: 10/818,491

(22) Filed: Apr. 5, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Diascia* plant named 'Codilav', characterized by its compact and upright plant habit; freely branching habit; freely flowering habit; light purple-colored flowers with red purple-colored centers; and good temperature tolerance.

1 Drawing Sheet

Botanical classification/cultivar designation: *Diascia×hybrida* cultivar Codilav.

BACKGROUND OF THE INVENTION

The present Invention relates to a new and distinct cultivar of *Diascia* plant, botanically known as *Diascia×hybrida,* and hereinafter referred to by the cultivar name Codilav.

The new *Diascia* is a product of a planned breeding program conducted by the Inventor in Cobbitty, New South Wales, Australia. The objective of the breeding program is to create new compact *Diascias* with numerous flowers and attractive flower coloration.

The new *Diascia* originated from a cross-pollination made by the Inventor in the spring of 2000 of the *Diascia× hybrida* cultivar Codiap, disclosed in U.S. Plant Pat. No. 13,169, as the female, or seed parent, with a proprietary *Diascia×hybrida* selection identified as X99.54.9, not patented, as the male, or pollen parent. The new *Diascia* was selected as a single plant from the resulting progeny of the cross-pollination by the Inventor in September, 2001, in an controlled environment in Cobbitty, New South Wales, Australia.

Asexual reproduction of the new cultivar by terminal cuttings in a controlled environment in Cobbitty, New South Wales, Australia since September, 2001 has shown that the unique features of this new *Diascia* are stable and reproduced true to type in successive generations.

SUMMARY OF THE INVENTION

Plants of the cultivar Codilav have not been observed under all possible environmental conditions. The phenotype may vary somewhat with variations in environment such as temperature and light intensity without, however, any variance in genotype.

The following traits have been repeatedly observed and are determined to be the unique characteristics of 'Codilav'. These characteristics in combination distinguish 'Codilav' as a new and distinct cultivar of *Diascia:*

1. Compact and upright plant habit.
2. Freely branching habit.

3. Freely flowering habit.
4. Light purple-colored flowers with red purple-colored centers.
5. Good temperature tolerance.

Plants of the new *Diascia* differ from plants of the female parent, the cultivar Codiap, in flower color as plants of the cultivar Codiap have soft orange-colored flowers. Plants of the new *Diascia* differ from plants of the male parent selection in flower color as plants of the male parent selection have pink-colored flowers.

Plants of the new *Diascia* can be compared to plants of the cultivar Strawberry Sundae, disclosed in U.S. Plant Pat. No. 11,488. In side-by-side comparisons conducted in Cobbitty, New South Wales, Australia, plants of the new *Diascia* differed from plants of the cultivar Strawberry Sundae in the following characteristics:

1. Plants of the new *Diascia* were more compact than plants of the cultivar Strawberry Sundae.
2. Plants of the new *Diascia* had larger flowers than plants of the cultivar Strawberry Sundae.
3. Plants of the new *Diascia* and the cultivar Strawberry Sundae differed in flower color as plants of the cultivar Strawberry Sundae had bright pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Diascia.*

The photograph at the top of the sheet comprises a side perspective view of a typical flowering plant of 'Codilav' grown in a container.

The photograph at the bottom of the sheet comprises a close-up view of typical flowers of 'Codilav'.

DETAILED BOTANICAL DESCRIPTION

The aforementioned photographs and following observations and measurements describe plants grown in Encinitas, Calif., in an outdoor nursery during the winter and spring with day temperatures averaging 24° C., night temperatures averaging 12° C., and light levels about 6,000 foot candles. Plants were grown for about 16 weeks with three plants per one-gallon container; plants were pinched one time.

Color references are made to The Royal Horticultural Society Colour Chart, 1995 Edition, except where general terms of ordinary dictionary significance are used.

Botanical classification: *Diascia×hybrida* cultivar Codilav.

Parentage:

*Female parent.*—*Diascia×hybrida* cultivar Codiap, disclosed in U.S. Plant Pat. No. 13,169.

*Male parent.*—Proprietary *Diascia×hybrida* selection identified as X99.54.9, not patented.

Propagation:

*Type cutting.*—Terminal vegetative cuttings.

*Time to initiate roots, summer and winter.*—About one week at 20° C.

*Time to produce a rooted young plant, summer and winter.*—About three weeks at 20° C.

*Root description.*—Fine, fibrous; white in color.

*Rooting habit.*—Freely branching; dense.

Plant description:

*Form.*—Upright and compact plant habit. Freely branching with lateral branches potentially forming at every node. Moderately vigorous growth habit.

*Plant height.*—About 20 cm.

*Plant diameter, single plant.*—About 16.5 cm.

*Lateral branches.*—Appearance: Thin, wiry; upright. Length: About 20 cm. Diameter: About 1.5 mm. Internode length: About 1.6 cm. Texture: Smooth, glabrous. Color: 144A.

*Foliage description.*—Arrangement: Opposite; simple. Length: About 2.3 cm. Width: About 1.8 cm. Shape: Deltoid to slightly cordate. Apex: Broadly acute. Base: Truncate to cordate. Margin: Slightly serrate. Texture, upper and lower surfaces: Smooth, glabrous. Venation pattern: Pinnate. Color: Developing foliage, upper surface: 146A. Developing foliage, lower surface: 146B. Fully expanded foliage, upper surface: 147A. Fully expanded foliage, lower surface: 147B. Venation, upper and lower surfaces: 147B. Petiole length: About 3 mm. Petiole diameter: About 2 mm. Petiole color: 144A.

Flower description:

*Flower type and habit.*—Solitary zygomorphic flowers arranged on terminal racemes. Five modified petals fused at base: two upper (banner) petals, two lateral petals, and one larger lower lip petal. Flowers not persistent. Flowers face mostly outwardly.

*Quantity.*—Freely flowering; typically about 18 to 20 buds and flowers per lateral branch.

*Natural flowering season.*—Plants typically flower during the spring in the Northern Hemisphere; flowering continuous during this period.

*Flower longevity on the plant.*—About four days.

*Fragrance.*—Not detected.

*Inflorescence size.*—Length: About 6.5 cm. Width: About 4 cm.

*Flower size.*—Length: About 2.3 cm. Width: About 2 cm. Depth: About 1.2 cm.

*Flower buds* (*showing color*).—Length: About 4 mm. Diameter: About 5 mm. Shape: Ovoid. Color: 75D.

*Petals.*—Quantity/arrangement: Five modified petals fused at base: two upper (banner) petals, two lateral petals, and one larger lower lip petal. Base of banner petals with concave yellow eyespots; lower surfaces of lateral petals modified into nectar spurs; and lower lip petal convex forming a roughly horizontal insect landing platform. Length: Banner petals: About 6 mm. Lateral petals: About 7 mm. Lower lip petal: About 1.2 cm. Width: Banner petals: About 5 mm. Lateral petals: About 8 mm. Lower lip petal: About 1.4 cm. Lateral petal spur: Length: About 6 mm. Diameter, at petal attachment: About 2 mm. Shape, all petals: Roughly spatulate. Apex, all petals: Rounded. Margin, all petals: Entire. Texture, all petals, upper and lower surfaces: Smooth, velvety. Color, all petals: When opening, upper surface: 62B. When opening, lower surface: 65D. Fully opened, upper surface: 75A; towards base, 72D; color becoming closer to 75B with development. Fully opened, lower surface: 75C to 75D. Nectar spurs: 77B. Eyespot on banner petals: 7A.

*Sepals.*—Arrangement/appearance: Single whorl of five sepals fused at base; star-shaped. Length: About 4 mm. Width: About 2 mm. Shape: Elliptic. Apex: Acute. Margin: Entire. Texture, upper and lower surfaces: Smooth, glabrous. Color, upper and lower surfaces: 144A.

*Peduncles.*—Length: About 1.75 cm. Width: About 1 mm. Angle: Upright to about 45° from vertical. Strength: Moderately strong. Texture: Smooth, glabrous. Color: 144A.

*Pedicels.*—Length: About 1.2 cm. Width: Less than 1 mm. Angle: About 45° from the peduncle. Strength: Moderately strong; slender. Texture: Smooth, glabrous. Color: 144A.

*Reproductive organs.*—Stamens: Quantity per flower: Four. Anther shape: Ovoid. Anther length: Less than 1 mm. Anther color: 12B. Pollen amount: Scarce. Pollen color: 12A. Pistils: Quantity per flower: One. Pistil length: About 4 mm. Style length: About 2 mm. Style color: 144D. Stigma shape: Rounded. Stigma color: 144D. Ovary color: 145A.

*Fruit/seed.*—Fruit and seed production has not been observed.

Disease/pest resistance: Plants of the new *Diascia* have not been noted to be resistant to pathogens or pests common to *Diascia*.

Temperature tolerance: Plants of the new *Diascia* have been observed to tolerate temperatures from 0 to 35° C.

It is claimed:

1. A new and distinct cultivar of *Diascia* plant named 'Codilav', as illustrated and described.

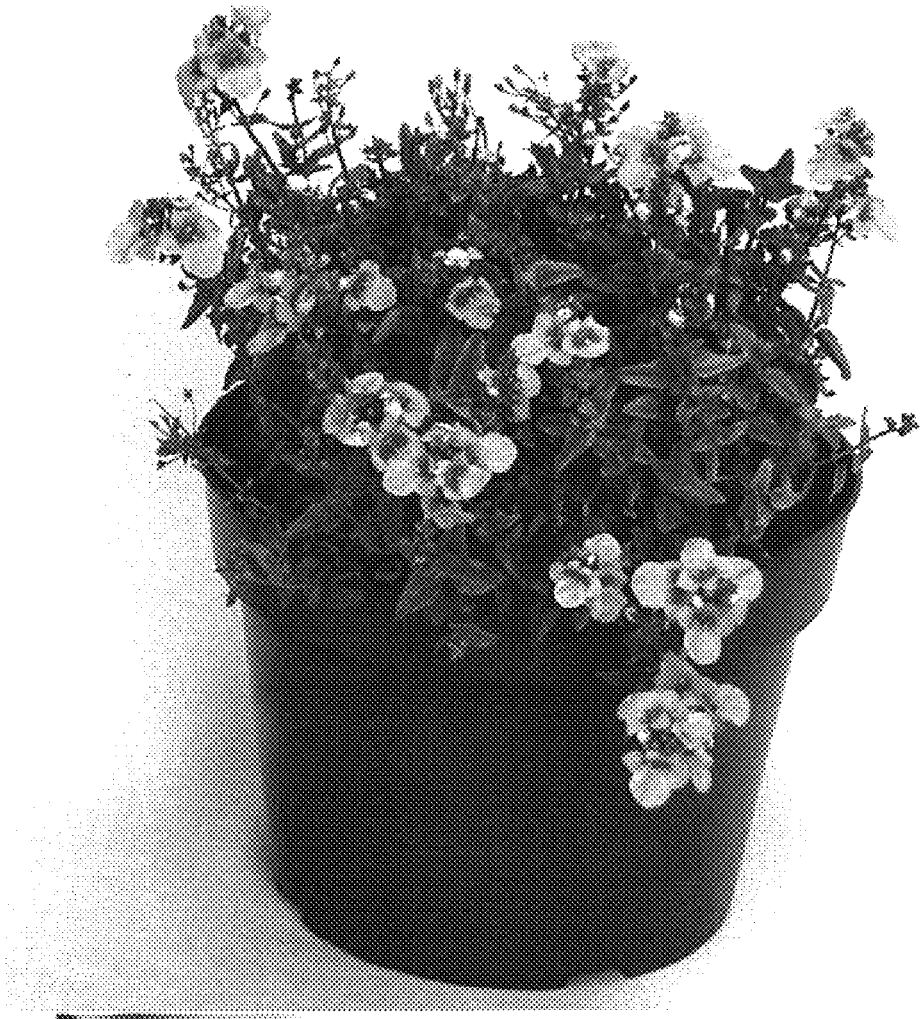
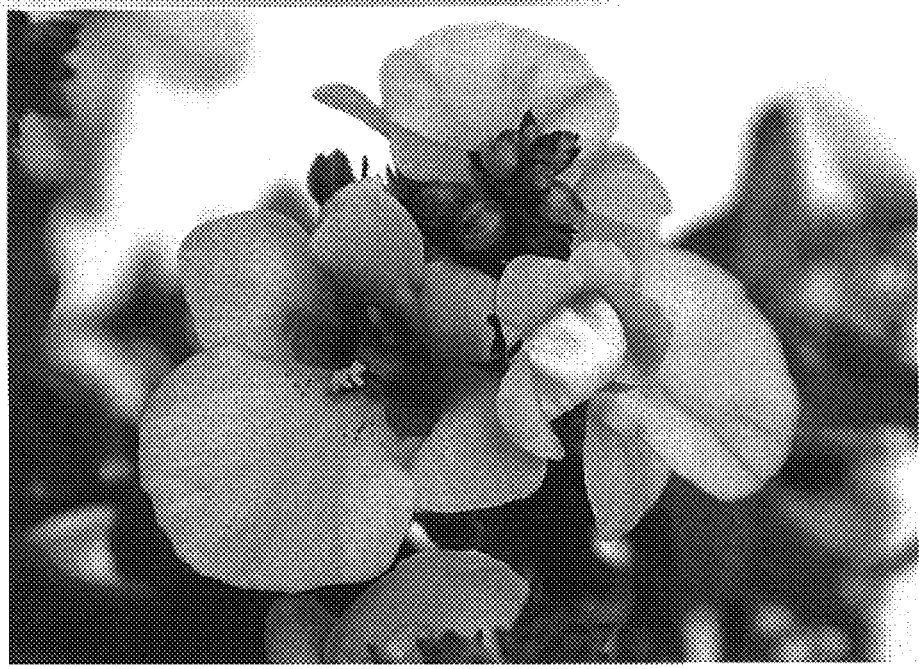

* * * * *